US008459792B2

(12) United States Patent
Wilson et al.

(10) Patent No.: US 8,459,792 B2
(45) Date of Patent: Jun. 11, 2013

(54) METHOD AND SYSTEMS FOR MEASURING INTERPUPILLARY DISTANCE

(76) Inventors: Hal E. Wilson, Raleigh, NC (US); James Welch, Raleigh, NC (US)

(*) Notice: Subject to any disclaimer, the term of this patent is extended or adjusted under 35 U.S.C. 154(b) by 184 days.

(21) Appl. No.: 13/094,349

(22) Filed: Apr. 26, 2011

(65) Prior Publication Data

US 2011/0267578 A1     Nov. 3, 2011

Related U.S. Application Data

(60) Provisional application No. 61/343,137, filed on Apr. 26, 2010.

(51) Int. Cl.
*A61B 3/10*     (2006.01)
(52) U.S. Cl.
USPC .......................................... 351/204; 351/246
(58) Field of Classification Search
USPC ........................................ 351/204, 246, 200
See application file for complete search history.

(56) References Cited

U.S. PATENT DOCUMENTS

| | | | |
|---|---|---|---|
| 4,730,260 | A | 3/1988 | Mori et al. |
| 6,095,650 | A | 8/2000 | Gao et al. |
| 6,142,628 | A | 11/2000 | Saigo |
| 6,535,223 | B1 | 3/2003 | Foley |
| 6,583,792 | B1 | 6/2003 | Agnew |
| 7,410,256 | B2 * | 8/2008 | Meyers ........................ 351/204 |

* cited by examiner

*Primary Examiner* — Hung Dang
(74) *Attorney, Agent, or Firm* — Caliber IP, LLC

(57) ABSTRACT

The proposed innovation provides methods and systems for measuring the interpupillary distance. The proposed innovation provides a fitting pad (102) having two detection points (104 and 106). The fitting pad is placed on the forehead of the user and an image is captured. The image is uploaded and pupil distance calculator software locates the fitting detection points and calculates the distance in pixels of the left and right X, Y coordinates. The software creates an image scale by dividing the pixel counts between the detection points. The software automatically locates the X, Y coordinates between the center of the left and right pupils and calculates the distance in pixels. The resulting pixel distance divided by the image scale provides the interpupillary distance in millimeter. In embodiments, segment height is calculated based upon an image imported by the user and the combined scaled images of the user and the frame.

20 Claims, 4 Drawing Sheets

```
Exemplary Fitting Pad Measurement Calculations

EYES
     Left    Right
  x   361    469              11,664.00
  y   264    258                  36.00
                              11,700.00
                                 108.17
                           PD =    53.524

FITTING PAD
     Left    Right
  x   359    460              10,201.00
  y   195    192                   9.00
                              10,210.00
                                 101.04
                      Pixels per MM    2.021

SIZE of
                      Fitting Pad    50.000   MM

= Input Values
```

METHOD AND SYSTEMS FOR MEASURING INTERPUPILLARY DISTANCE

FIELD OF THE INNOVATION

The present innovation relates to a methods and systems for measuring interpupillary distance. More specifically, the innovation relates to a computer aided methods and systems for measuring interpupillary distance with minimal manual interference.

BACKGROUND OF THE INVENTION

Interpupillary Distance (IPD) is the distance between the centers of the pupils in each eye. This measurement is used when preparing to make prescription eyeglasses. Positioning lenses correctly in relation to the centre of the pupils is especially important for higher powered lenses due to the location of the optical centre of the lenses.

However, it is very difficult to manually take this measurement against two moving objects (left and right eye) and almost impossible to measure ones own pupillary distance.

As examples of known art, I refer to U.S. Pat. No. 7,322,697 wherein there is disclosed a method of measuring a pupil distance. The method includes locating an imaging device at a position a predetermined distance away from a member attached to eyeglasses worn by a subject. The member has two indicators. The method further includes photographing the subject while the subject observes an observing point in the vicinity of the imaging device, measuring an apparent distance between left and right pupils of the subject on a photographed image, and obtaining an interpupillary distance PD in accordance with:

$$PD=[(A+B) \times C \times E]/(A \times D) \qquad (1)$$

where "A" represents a distance between the member and the imaging device, "B" represents a distance between a center of rotation of each eye of the subject and the member, "C" represents an actual distance between the indicators in a direction parallel with a line connecting left and right centers of rotation of the subject, "D" represents an apparent distance between the indicators in the direction parallel with the line connecting the left and right centers of rotation on the photographed image, and "E" represents the apparent distance between the left and right pupils of the subject on the photographed image.

Again in U.S. Pat. No. 5,822,032, a device for measuring the interpupillary distance between the pupils of the eyes of that person is disclosed. The device includes a frame having a face and a first hole extending through the frame from the face which is positional at one of the person's two pupils. A disk is mounted juxtaposed to the frame which is rotatable about an axis perpendicular to the frame's face. The disk has a surface and a plurality of second holes extending through the disk from its surface. By rotating the disk, one of the second holes is positional at the other of the person's pupils. The interpupillary distance (IPD) is equal or approximately equal to the distance between the centers of the first and second holes when the holes are positioned at the person's respective pupils.

Again in U.S. Pat. No. 6,535,223, a method for determining the real-world interpupillary distance is provided. The method includes determining the interpupillary distance for a user from an image provided for use with "virtual try-on" technology. This is accomplished by having the user place a reference object on or near their face in the virtual try-on image. The reference object should be one that is a standard size and is readily available to users. Alternatively, the reference object used can be the iris in a user's own eye, since it is well known that the human iris is of a relatively fixed size from individual to individual. When using a reference object, the user takes the facial picture with the reference object on generally the same plane and distance from the camera as their face, such as by holding a quarter on their chin with a single finger. The image is then submitted to the web site as is now standard with sites utilizing virtual try-on technology. After the image is transmitted, the image can then be resized and used to try-on different frames as is known in the prior art. Alternatively, a second image without a reference object can be used for trying on frames. Once the frames are selected and an order for the frames placed, the image with the reference object is associated with the order. The width of the reference object on the image is then compared to the measured interpupillary distance on the image. These measurements can be made in pixels as opposed to real-world distances, because the image is being provided in a pixilated digital file. The actual interpupillary distance can then be calculated by comparing the ratio of the distances measured in the image with the known width of the reference object. Similarly, the virtual interpupillary distance or segment height (usually called "seg height") needed for multi-focal elements can be determined by measuring the height using the frame on face virtual try-on technology. The measured distance on the image is converted to a real world measurement using the ratio obtained from the reference image.

All of these stated methods and devices/systems and some other methods and devices/systems presently known in the art have had some flaws in design or mechanism and lacks precision. Most of the existing devices are too expensive to be practical for most users. Some shortfalls of the existing methods and systems include manual interference, leading to inaccuracy in measurements. In light of this, there is a need for a method and system that overcomes these constraints.

SUMMARY

The present innovation is directed to methods and systems for measuring the interpupillary distance. The proposed innovation provides a fitting pad having two detection points. The fitting pad is placed on the forehead of the user and an image is captured. The captured image is uploaded and pupil distance calculator software automatically locates the fitting detection points and calculates the distance in pixels of the left and right X, Y coordinates. The said software creates an image scale by dividing the pixel counts between the detection points. The said software automatically locates the X, Y coordinates between the center of the left and right pupils and calculates the distance in pixels. The resulting pixel distance divided by the image scale provides the interpupillary distance in millimeter.

In embodiments, the distance between the detection points is at least 40 mm. In embodiments, the detection points are printed on a specialized fitting frame or a custom trial frame and the detection points are located at a consistent, fixed distance.

In embodiments, the detection points are printed in such a manner so that there is a high level of contrast between the detection points and the fitting pad surface.

In embodiments, the detection points are located by the difference in level of contrast. In embodiments, the detection points are located by their respective shape and size.

In embodiments, the centres of the left and right eye pupil are located by an attribute associated with the image of the eye. In embodiments, the fitting pad is provided in a pre-printed format or can be printed by a user on a personal computer.

In embodiments, the fitting pad can be of different sizes. In embodiments, the size of the fitting pad is based on the age of the user or some other similar attributes of the user.

In addition to the interpupillary distance, other measurements such as segment height are calculated which are required while manufacturing multi-focal lenses.

BRIEF DESCRIPTION OF FIGURES

The systems and methods described herein may be understood by reference to the following figures:

FIG. 3 depicts a table showing exemplary calculations for measuring the interpupillary distance in accordance with various embodiments of the present innovation.

While the above-identified figures set forth preferred embodiments of the innovation, other embodiments are also contemplated, as noted in the discussion. In all cases, this disclosure presents the present innovation by way of representation and not limitation. It should be understood that numerous other modifications and embodiments can be devised by those skilled in the art which fall within the scope and spirit of the principles of this innovation.

DETAILED DESCRIPTION OF FIGURES

Figure 1:
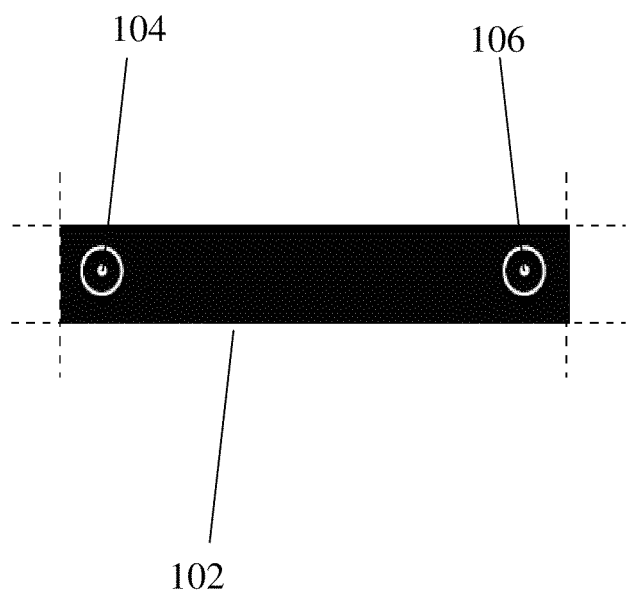
FIG. 1 illustrates a fitting pad in accordance with various embodiments of the present innovation.

Referring now to the drawings where the showings are for the purpose of describing the preferred embodiment of the proposed innovation and not for limiting the same, FIG. 1 illustrates a fitting pad 102. The fitting pad 102 along with the other system elements and method steps enables the accurate measurement of the interpupillary distance.

In an embodiment of the present innovation, the fitting pad 102 can be provided in a pre-printed format or printed by a user on a personal computer, laptop, and the like. In an embodiment of the present innovation, the fitting pad 102 can be of different sizes. Fitting pad 102 of different sizes can be made based on the age of the user or some other similar attributes of the user.

The fitting pad 102 has two detection points 104 and 106. The detection points 104 and 106 are on the ends of the fitting pad 102 and are designed to reduce errors in determining the exact end points. In an embodiment of the present innovation, the distance between the detection points 104 and 106 is at least 30 mm. In an embodiment of the present innovation, the fitting pad detection points 104 and 106 can also be printed on a specialized fitting frame or a custom trial frame where the detection points 104 and 106 are located at a consistent, fixed distance. The detection points 104 and 106 are printed in such a manner so that there is a high level of contrast between the detection points 104 and 106 and the fitting pad 102 surfaces.

Figure 2:
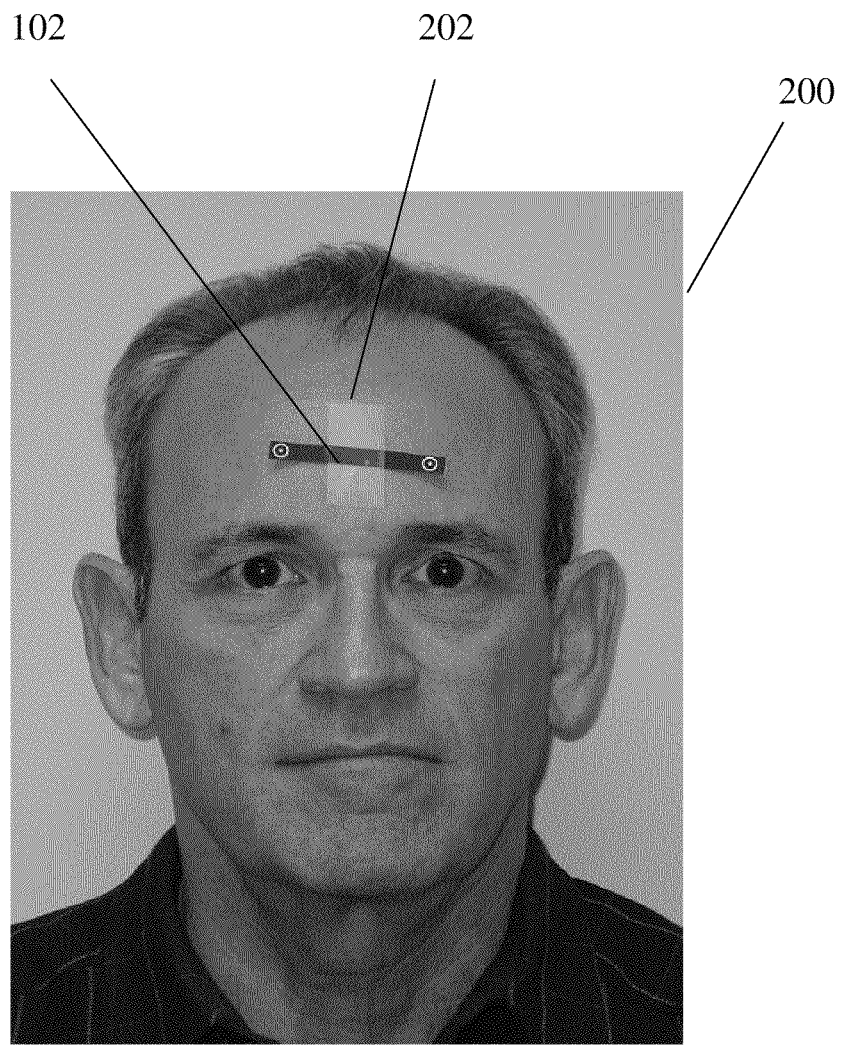
FIG. 2 depicts the fitting pad being placed on the forehead of the user in accordance with various embodiments of the present innovation.

Referring to FIG. 2, the fitting pad 102 is placed on the forehead of the user. In an embodiment of the present innovation, a tape 202 may be attached on the center to make the fitting pad stick to the forehead of the user. In an embodiment of the present innovation, a photo 200 focusing the eyes of the user and his forehead having the fitting pad 102 is captured. A known person in the vicinity of the user can capture the photo 200.

In an embodiment of the present innovation, pupil distance calculator software imports the photo 200. The photo distance calculator software 200 automatically locates the fitting detection points 104 and 106 of the fitting pad 102. As there is a high level of contrast between the detection points 104 and 106 and the fitting pad 102 surface, the pupil distance calculator identify these detection points based on the level of contrast. In another embodiment of the present invention, the pupil distance calculator software may also use the shape or geometry of the detection points 104 and 106 in addition or in conjunction with the contrast element. It may be noted that pupil distance calculator software of the proposed innovation is explained to locate the detection points 104 and 106 on the fitting pad 102 by using the difference in the level of contrast, the shape or geometry of the detection points 104 and 106; however, those skilled in the art would appreciate that the detection points 104 and 106 can be located by any technology presently known in the art.

On identifying the detection points 104 and 106, the pupil distance calculator software calculates the distance between the detection point 104 and 106 in pixels by tracking their respective X, Y coordinates. In an exemplary scenario, the X, Y coordinate of the detection point 104 can be 359 and 195 respectively. The X, Y coordinates of the detection point 106 can be 460 and 192 respectively. So, the distance in pixels between the two detection points will be 101.04. In an embodiment of the present invention, to determine the number of pixels between the two detection points on the fitting pad 102 when the detection points 104 and 106 are not perfectly horizontal; calculations are performed using Pythagorean Theorem. For a right triangle, the square of the hypotenuse is equal to the sum of the squares of the other two sides. Thus, for two points in a pixilated digital image, with each point having an x and y coordinate, the number of pixels between the selected points will be square root of the difference of the x coordinates squared plus the difference of the y coordinates squared.

In an embodiment of the present innovation, the pupil distance calculator software creates an image scale. In this embodiment of the present innovation, the image scale is created by dividing the above calculated pixel counts between the detection points 104 and 106 with the already known distance of the detection points 104 and 106 (say 50 mm in this case). In the above stated scenario, the image scale will be 2.021 pixels per mm (101.04/50).

In an embodiment of the present innovation, the pupil distance calculator software also automatically locates the X, Y coordinates between the center of the left and right pupils. The pupil distance calculator software locates the X; Y coordinates of the center of the left and right pupil based on the identification of the size of eye, level of contrast, and the like. It may be noted that pupil distance calculator software of the proposed innovation is explained to center of the left and right pupil by using the difference in the level of contrast, shape and size of the eye, and the like; however, those skilled in the art would appreciate that the center of the left and right pupil can be located by any technology presently known in the art.

Once the centers of the left and right pupil are located, the distance between them in pixels is calculated. In the above stated example, the X, Y coordinate of the user's left eye is 361 and 264 respectively and the X, Y coordinate of the user's right eye is 469 and 258 respectively. So, the distance in pixels between the centers of the left and right pupil is 108.17.

In an embodiment of the present innovation, the resulting pixel distance divided by the image scale is the pupilary distance in mm. In the above stated example, the pupilary distance will be 53.524 (108.17/2.021). This pupilary distance of the user can be used to fit eyeglasses. In an embodiment of the present invention, to determine the number of pixels between the two detection points on the fitting pad 102 and the distance between the pupils when the detection points 104 and 106 are not perfectly horizontal, calculations are performed using Pythagorean theorem. For a right triangle, the square of the hypotenuse is equal to the sum of the squares of the other two sides. Thus, for two points in a pixilated digital image, with each point having an x and y coordinate, the number of pixels between the selected points will be square root of the difference of the x coordinates squared plus the difference of the y coordinates squared.

It may be noted that a table 300 showing the calculations in the above stated example has been shown in the FIG. 3. Note that the calculations shown in the above stated example is just for explaining the innovation in a simplistic manner and should not be taken in a limiting sense.

Figure 4:
FIG. 4 depicts the loaded image on a web portal in accordance with various embodiments of the present innovation.

In an embodiment of the present innovation, when the pupil distance is known, the image can be used to load to a web portal as shown in FIG. 4. The image is loaded on web-portal to try out different frames. The web portal contains frontal frame images that are sized to a constant scale, for example 2 pixels=1 mm. When the user image is loaded to the web portal, the subject image is resized to the same scale. In this case, the pupils are used as the scaling points. For example, if a user has a real life pupil distance of 60 mm, then the uploaded user image would be resized so that there are 120 pixels (60 mm/Constant Scale of 2) between the left and right eye X,Y coordinates. The user can try on different frames by superimposing the frame or sunglass on top of the subjects face. The resulting combined image is an accurate representation of the real life sizes.

The resulting combined image is an accurate representation of the real life sizes. This consistent scale allows the user to calculate the distance between any 2 points in the combined image. In addition to the interpupillary distance, other measurements are needed when manufacturing multi-focal lenses.

As presently known in the art, all lenses with additional elements in them such as bifocals, trifocals, and progressive lenses are considered multi-focal lenses. In These lenses may need a measurement known as the segment or "seg" height. The seg height is the distance from the bottom of the selected frame to the top of the multi-focal segment.

In an embodiment of the present innovation, eyeglass retailers and opticians make a determination where the seg height should be located based upon the location of the eyes in the frames (the combined image). Generally, bifocal lens elements are placed so that the seg height is at the lower lid of the eye; a tri-focal seg height would be at the bottom of the pupil. Progressive lenses have a seg height that is approximately the same as the vertical pupillary distance between the center of the pupil and the bottom of the frame.

The present innovation allows prescription eyewear retailers to determine the interpupillary and the seg height based upon an image imported by the user and the combined scaled images of the user and the frame.

In an embodiment of the present innovation, the fitting pad 102 is specifically not round in shape as the round object is more difficult to measure. In addition, the round object can only be 10-20 mm in width; the margin for error is very high. If the user selects points that are 1 mm in error, the resulting pupilary distance calculations can vary by 10% or more.

Although the present innovation has been described in considerable detail with reference to certain preferred versions thereof, other versions are possible. Therefore, the spirit and scope of the appended claims should not be limited to the description of the preferred versions described herein.

All features disclosed in the specification, including the claims, abstracts and drawings, and all the steps in any method or process disclosed, may be combined in any combination except a combination where at least some of such features and/or steps are mutually exclusive. Each feature disclosed in the specification, including the claims, abstract, and drawings, can be replaced by alternative features serving the same, equivalent or similar purpose, unless expressly stated otherwise. Thus, unless expressly stated otherwise, each feature disclosed is one example only of a generic series of equivalent or similar features.

Any element in a claim that does not explicitly state "means" for performing a specified function or "step" for performing a specified function, should not be interpreted as a "means" or "step" clause as specified in 35 U.S.C. §112.

All documents referenced herein are hereby incorporated by reference.

What I claim is:

1. A method for measuring the interpupillary distance, the method comprising;
   providing a fitting pad having two detection points;
   placing the fitting pad on the forehead of the user;
   capturing and uploading the image of the user; and
   providing pupil distance calculator software; the said software is configured for automatically locating the fitting detection points;
   calculating the distance in pixels of the left and right X, Y coordinates;
   creating an image scale by dividing the pixel counts between the detection points;
   automatically locating the X, Y coordinates between the center of the left and right pupils; and
   calculating the distance in pixels between the center of the left and right pupils.

2. The method as recited in claim 1, wherein the distance between the detection points is at least 40 mm.

3. The method as recited in claim 1, wherein the detection points are printed on a specialized fitting frame or a custom trial frame; and wherein the detection points are located at a consistent, fixed distance.

4. The method as recited in claim 1, wherein the detection points are printed in such a manner so that there is a high level of contrast between the detection points and the fitting pad surface.

5. The method as recited in claim 1, wherein the detection points are located by at least one of the difference in level of contrast, shape and size of the detection points.

6. The method as recited in claim 1, wherein the centre of the left and right eye pupil are located by an attribute associated with the image of the eye.

7. The method as recited in claim 1, wherein the fitting pad is provided in a pre-printed format or can be printed by a user on a personal computer.

8. The method as recited in claim 1, wherein the fitting pad can be of different sizes.

9. The method as recited in claim 1, wherein segment height is calculated based upon an image imported by the user and the combined scaled images of the user and the frame.

10. A system for measuring the interpupillary distance, the method comprising;
    a fitting pad having two detection points, the fitting pad being placed on the forehead of the user;

a camera for capturing and uploading the image of the user; and a pupil distance calculator software; the said software is configured for automatically locating the fitting detection points;

calculating the distance in pixels of the left and right X, Y coordinates;

creating an image scale by dividing the pixel counts between the detection points;

automatically locating the X,Y coordinates between the center of the left and right pupils; and calculating the distance in pixels between the center of the left and right pupils.

11. The system as recited in claim 10, wherein the distance between the detection points is at least 40 mm.

12. The system as recited in claim 10, wherein the detection points are printed on a specialized fitting frame or a custom trial frame; and wherein the detection points are located at a consistent, fixed distance.

13. The system as recited in claim 10, wherein the detection points are printed in such a manner so that there is a high level of contrast between the detection points and the fitting pad surface.

14. The system as recited in claim 10, wherein the detection points are located by the difference in level of contrast, shape and size of the detection points.

15. The system as recited in claim 10, wherein the centre of the left and right eye pupil are located by an attribute associated with the image of the eye.

16. The system as recited in claim 10, wherein segment height is calculated based upon an image imported by the user and the combined scaled images of the user and the frame.

17. A system for fitting a user with a pair of glasses, the system comprising:

a fitting pad configured to be placed on the forehead of the user, the fitting pad having a first detection point and a second detection point at a predetermined distance from the first detection point;

a camera for capturing an image of the user, including the user's pupils, as the user wears the fitting pad;

a display;

a user interface; and a processor in communication with the display, the user interface, and the camera;

wherein the processor is configured to calculate the number of pixels on the image between the first and second detection points, so as to provide a pixels-per-distance calculation for the captured image.

18. The system of claim 17, wherein the system is further configured to prompt the user to confirm the location of the first and second detection points on the image.

19. The system of claim 17, wherein the system is further configured to prompt the user to confirm the location of the user's pupils on the image.

20. The system of claim 19, wherein the system uses the confirmed location of the user's pupils to present a virtual image of the user wearing a pair of glasses.

* * * * *